US010869985B2

(12) United States Patent
Rothermel

(10) Patent No.: US 10,869,985 B2
(45) Date of Patent: Dec. 22, 2020

(54) FLOW MEMBER

(71) Applicant: KONINKLIJKE PHILIPS N.V., Eindhoven (NL)

(72) Inventor: Justin Edward Rothermel, Monroeville, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 332 days.

(21) Appl. No.: 15/559,468

(22) PCT Filed: Mar. 24, 2016

(86) PCT No.: PCT/EP2016/056482
§ 371 (c)(1),
(2) Date: Sep. 19, 2017

(87) PCT Pub. No.: WO2016/156176
PCT Pub. Date: Oct. 6, 2016

(65) Prior Publication Data
US 2018/0104434 A1 Apr. 19, 2018

Related U.S. Application Data

(60) Provisional application No. 62/140,487, filed on Mar. 31, 2015.

(30) Foreign Application Priority Data

May 13, 2015 (EP) .................................. 15167477

(51) Int. Cl.
*A61M 16/08* (2006.01)
*G01F 1/40* (2006.01)
(Continued)

(52) U.S. Cl.
CPC ......... *A61M 16/0858* (2014.02); *A61B 5/087* (2013.01); *A61M 16/00* (2013.01);
(Continued)

(58) Field of Classification Search
CPC .......... A61M 16/0858; A61M 16/0057; A61M 16/16; A61M 2016/0036;
(Continued)

(56) References Cited

U.S. PATENT DOCUMENTS 3,559,482 A * 2/1971 Baker et al. .......... G01F 1/6847
73/202.5
4,118,973 A * 10/1978 Tucker ...................... G01F 1/42
73/54.04

(Continued)

FOREIGN PATENT DOCUMENTS

| CN | 101311683 A | 11/2008 |
| CN | 104258491 A | 1/2015 |
| WO | 2007024956 A2 | 3/2007 |

OTHER PUBLICATIONS

G. K. Sahu, Handbook of Piping Design, 1998, New Age International, p. 21 (Year: 1998).*

*Primary Examiner* — Joseph D. Boecker
*Assistant Examiner* — Thomas W Greig

(57) ABSTRACT

A flow member (200) is for a flow assembly (100) of a pressure support system (2). The pressure support system includes a patient interface device (6), a flow generator (4), and a coupling conduit (8). The flow assembly includes a cover (102) and a sensing assembly (110). The sensing assembly has a flow sensor (114) having flow sensing components (118,120). The flow member comprises: a body (202) comprising: a mounting portion (204) connected to the cover, thereby enclosing the sensing assembly, a gas conduit (206) at least partially overlaying the mounting portion, the second conduit fluidly coupling the first conduit to the flow
(Continued)

generator, and a number of flow conduits (208,210) each extending transverse to the gas conduit (206) and receiving a corresponding flow sensing component. Each flow conduit terminates at a distal end portion (209,211) in fluid communication with the gas conduit (206), each distal end portion being spaced a distance from the gas conduit (206) and located internal with respect thereto.

20 Claims, 11 Drawing Sheets

(51) Int. Cl.
*G01F 15/12* (2006.01)
*G01F 15/00* (2006.01)
*G01F 1/50* (2006.01)
*G01F 1/684* (2006.01)
*A61M 16/00* (2006.01)
*A61B 5/087* (2006.01)
*A61M 16/16* (2006.01)

(52) U.S. Cl.
CPC ...... *A61M 16/0057* (2013.01); *A61M 16/021* (2017.08); *A61M 16/16* (2013.01); *G01F 1/40* (2013.01); *G01F 1/50* (2013.01); *G01F 1/6842* (2013.01); *G01F 15/00* (2013.01); *G01F 15/12* (2013.01); *G01F 15/125* (2013.01); *A61B 2562/18* (2013.01); *A61M 2016/0027* (2013.01); *A61M 2016/0036* (2013.01); *A61M 2205/3331* (2013.01); *A61M 2205/3334* (2013.01); *A61M 2206/11* (2013.01)

(58) Field of Classification Search
CPC .... A61M 2016/0027; G01F 1/40; G01F 1/08; G01F 1/80; G01F 1/6842; G01F 5/005; G05D 7/06; F17D 1/16; A61B 5/087
See application file for complete search history.

(56) References Cited

U.S. PATENT DOCUMENTS

| | | | | |
|---|---|---|---|---|
| 5,088,332 | A * | 2/1992 | Merilainen | A61B 5/0833 600/538 |
| 5,631,417 | A * | 5/1997 | Harrington | B82Y 15/00 73/204.26 |
| 6,322,247 | B1 * | 11/2001 | Bonne | G01F 1/6842 374/138 |
| 6,601,460 | B1 * | 8/2003 | Materna | G01F 1/40 73/861.52 |
| 6,655,207 | B1 * | 12/2003 | Speldrich | G01F 1/40 73/202.5 |
| 7,059,184 | B2 * | 6/2006 | Kanouda | G01F 1/6842 73/202.5 |
| 7,302,862 | B2 * | 12/2007 | Fujiwara | G01F 1/684 73/861.52 |
| 7,337,678 | B2 * | 3/2008 | Thakre | A61B 5/0876 73/861.52 |
| 7,340,966 | B2 * | 3/2008 | DiMatteo | G01F 1/42 137/39 |
| 7,878,980 | B2 * | 2/2011 | Ricciardelli | A61B 5/091 600/529 |
| 8,826,731 | B2 * | 9/2014 | Speldrich | F17D 1/00 73/204.21 |
| 2004/0016302 | A1 * | 1/2004 | Misholi | A61B 5/087 73/861.53 |
| 2006/0101901 | A1 * | 5/2006 | Klammler | G01F 1/40 73/61.53 |
| 2008/0072979 | A1 * | 3/2008 | Rosenbaum | F02M 35/10118 138/39 |
| 2009/0211371 | A1 * | 8/2009 | Lewis | G01F 1/363 73/861.63 |
| 2010/0163119 | A1 | 7/2010 | Isobe et al. | |
| 2016/0370213 | A1 * | 12/2016 | Stromsten | G01F 1/40 |

\* cited by examiner

FLOW MEMBER

CROSS-REFERENCE TO PRIOR APPLICATIONS

This application is the U.S. National Phase application under 35 U.S.C. § 371 of International Application Serial No. PCT/EP2016/056482, filed on 24 Mar. 2016, which claims the benefit of U.S. Application Ser. No. 62/140,487, filed on 31 Mar. 2015 and European Application No. 15167477.7, filed on 13 May 2015. These applications are hereby incorporated by reference herein.

FIELD OF THE INVENTION

The present invention relates to non-invasive ventilation and pressure support systems wherein a patient interface device is used to deliver a flow of breathing gas to a patient. The present invention also relates to flow assemblies for pressure support systems and, more particularly, to flow assemblies having sensing assemblies. The present invention further relates to flow members for flow assemblies.

BACKGROUND OF THE INVENTION

U.S. Pat. No. 6,655,207 discloses an integrated module for measuring a flow rate of a fluid, whether gaseous or liquid, with a flow restrictor comprising a plurality of orifices adapted to a flow channel of the integrated module and a sensor mounted to measure a property of the fluid at said flow restrictor corresponding to the flow rate. The integrated module provided may be used in numerous flow systems, such as reactors, ventilators and respirators, and has the benefit of better laminarization of the flow as well as better calibration between the flow sensor and the flow restrictor for more accurate flow measurements. It may be desirable, under high flow operating conditions, to deploy extensions to the inlet end and outlet end of the sensing tap. Exemplary extensions are narrow hollow tubes. These tubes magnify the pressure differential across the sensing channel and further restrict the flow entering the sensing channel to prevent damage and reduce noise that could result from high flow rates. The tubes have a hollow core with a diameter approximately equal to that of the ends and are aligned to extend the same distance into the channel from each respective end.

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

During therapy, it is important to monitor any one of a number of parameters (e.g., without limitation, pressure and flow rate). As a result, pressure support systems typically employ various sensors to monitor the parameters.

SUMMARY OF THE INVENTION

It is an object of the invention to reduce sensor failure. The invention is defined by the independent claims. The dependent claims define advantageous embodiments.

The invention is based on the recognition that it is common to humidify the breathing gas before delivering it to the airway of the patient, and that gases exhaled by the patients typically contain significant moisture. Post humidification water ingress and moisture ingress from exhaled gases in sensors is a significant cause of sensor failure. The invention ensures that moisture can less easily reach the sensor, the notion "moisture" being used to cover both post-humidification water and moisture in exhaled gases.

In one embodiment, a flow member for a flow assembly of a pressure support system is provided. The pressure support system includes a patient interface device, a gas flow generator structured to produce a flow of breathing gas for a patient, and a first coupling conduit coupled to each of the gas flow generator and the patient interface device. The flow assembly includes a cover and a sensing assembly. The sensing assembly includes a flow sensor having a number of flow sensing components. The flow member comprises: a body comprising: a mounting portion structured to be connected to the cover, thereby enclosing the sensing assembly, a second coupling conduit at least partially overlaying the mounting portion, the second coupling conduit being structured to fluidly couple the first coupling conduit to the gas flow generator, and a number of flow conduits each extending transverse to the second coupling conduit and being structured to receive a corresponding one of the flow sensing components. Each of the flow conduits terminates at a distal end portion in fluid communication with the second coupling conduit, each distal end portion being spaced a distance from the second coupling conduit and located internal with respect thereto.

In another embodiment, a flow assembly for a pressure support system is provided. The pressure support system includes a patient interface device, a gas flow generator structured to produce a flow of breathing gas for a patient, and a first coupling conduit coupled to each of the gas flow generator and the patient interface device. The flow assembly comprises: a cover; a sensing assembly comprising a flow sensor having a number of flow sensing components; and a flow member comprising: a body comprising: a mounting portion connected to the cover, thereby enclosing the sensing assembly, a second coupling conduit at least partially overlaying the mounting portion, the second coupling conduit being structured to fluidly couple the first coupling conduit to the gas flow generator, and a number of flow conduits each extending transverse to the second coupling conduit and receiving a corresponding one of the flow sensing components. Each of the flow conduits terminates at a distal end portion in fluid communication with the second coupling conduit, each distal end portion being spaced a distance from the second coupling conduit and located internal with respect thereto.

In another embodiment, a pressure support system is provided. The pressure support system comprises: a patient interface device; a gas flow generator structured to produce a flow of breathing gas for a patient; a first coupling conduit coupled to each of the gas flow generator and the patient interface device; and a flow assembly comprising: a cover, a sensing assembly comprising a flow sensor having a number of flow sensing components, and a flow member comprising: a body comprising: a mounting portion connected to the cover, thereby enclosing the sensing assembly, a second coupling conduit at least partially overlaying the mounting portion, the second coupling conduit fluidly coupling the first coupling conduit to the gas flow generator, and a number of flow conduits each extending transverse to the second coupling conduit and receiving a corresponding one of the flow sensing components. Each of the flow conduits terminates at a distal end portion in fluid communication with the second coupling conduit, each distal end portion being spaced a distance from the second coupling conduit and located internal with respect thereto.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
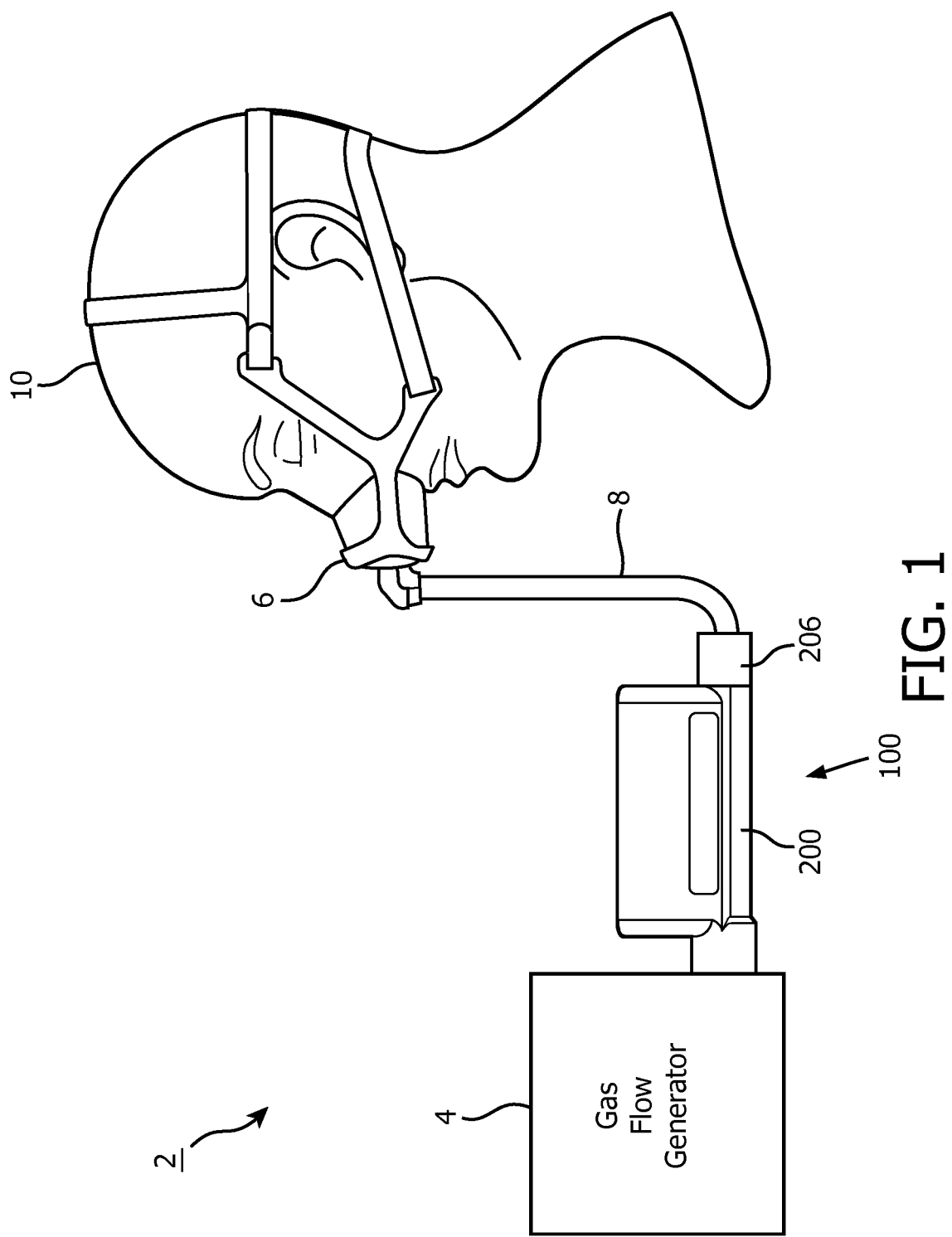
FIG. 1 is a simplified view of a pressure support system, in accordance with one aspect of the disclosed concept.

For purposes of the description hereinafter, directional phrases used herein such as, for example, "up", "down", "above", "below" and derivatives thereof shall relate to the disclosed concept, as it is oriented in the drawings. It is to be understood that the specific elements illustrated in the drawings and described in the following specification are simply exemplary embodiments of the disclosed concept. Therefore, specific orientations and other physical characteristics related to the embodiments disclosed herein are not to be considered limiting with respect to the scope of the disclosed concept.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

FIG. 1 shows a simplified view of a pressure support system 2, in accordance with one aspect of the disclosed concept. Pressure support system 2 includes a gas flow generator 4 (shown in simplified form), a patient interface device 6, and a coupling conduit 8 (shown in simplified form) coupled to each of gas flow generator 4 and patient interface device 6 to provide fluid communication therebetween. In operation, gas flow generator 4 generates a flow of breathing gas to be delivered to the airway of a patient 10. As will be discussed in greater detail blow, pressure support system 2 further includes a flow assembly 100 coupled to each of gas flow generator 4 and coupling conduit 8. Flow assembly 100 monitors various parameters of gas flow (e.g., without limitation, pressure and volumetric flow rate of gas) and advantageously protects sensing equipment from undesirable exposure to water and/or moisture from exhaled gases by patient 10.

Figure 2:
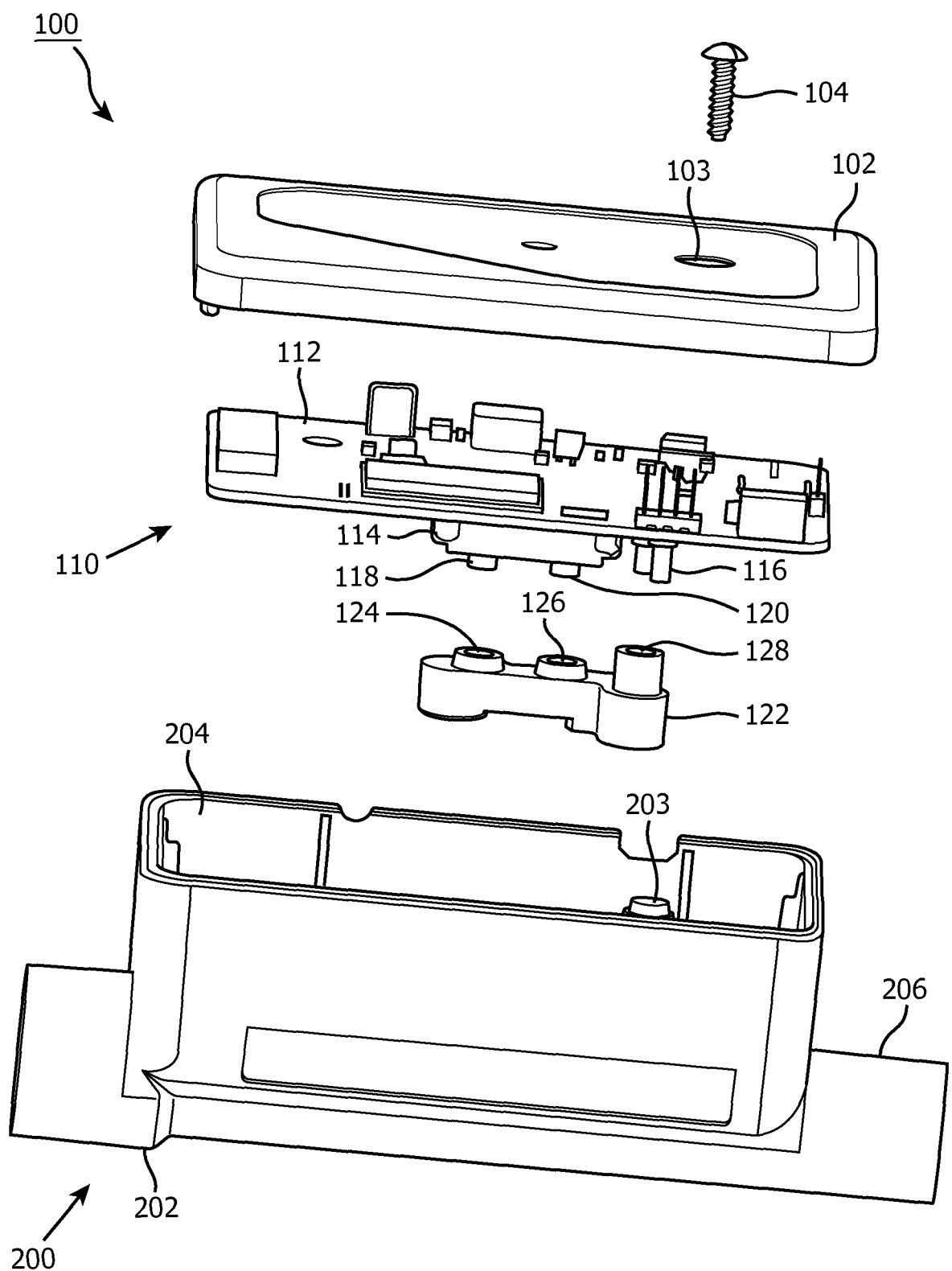
FIG. 2 is an exploded perspective view of a flow assembly for the pressure support system of FIG. 1.

FIG. 2 shows an exploded view of flow assembly 100. As shown, flow assembly 100 includes a cover 102, a coupling member 104, a sensing assembly 110, and a flow member 200. Sensing assembly 110 is coupled to each of cover 102 and flow member 200 and in operation is enclosed by (i.e., is located internal) cover 102 and flow member 200. Sensing assembly 110 includes an electrical component 112, a flow sensor 114, a pressure sensor 116, and a sealing gasket 122. Flow sensor 114 and pressure sensor 116 are each connected to electrical component 112. Furthermore, flow sensor 114 includes a number of flow sensing components (see, for example, two flow sensing components 118,120) that together operate to measure volumetric flow rate of gas in a manner generally well known in the art. Specifically, each of flow sensing components 118,120 has access to breathing gas flowing through flow member 200 at different locations. Continuing to refer to FIG. 2, sealing gasket 122 has a number of thru holes (see, for example, three thru holes 124,126,128). It will be appreciated that each of flow sensing component 118, flow sensing component 120, and pressure sensor 116 is aligned with (i.e., overlays and/or partially extends into) a corresponding one of thru holes 124,126,128.

Flow member 200 includes a body 202 that has a mounting portion 204, a gas conduit 206, and a cylindrical-shaped protrusion 203 (see also, for example, FIG. 3 and FIG. 4) extending outwardly from gas conduit 206. Gas conduit 206 at least partially overlays mounting portion 204 and preferably extends through mounting portion 204. Gas conduit 206 fluidly couples gas flow generator 4 (FIG. 1) to conduit 8 (FIG. 1). In other words, breathing gas generated by flow generator 4 (FIG. 1) flows through gas conduit 206 and into coupling conduit 8 (FIG. 1) in order to be delivered to patient 10 (FIG. 1). Furthermore, as will be discussed below, each of pressure sensor 116 and flow sensing components 118,120 has access to the breathing gas flowing through gas conduit 206 in order to monitor the pressure and volumetric flow rate of gas, respectively. Additionally, in operation, coupling member 104 extends through a thru hole 103 in cover 102 and at least partially into cylindrical-shaped protrusion 203 in order to connect cover 102 to mounting portion 204, thereby enclosing sensing assembly 110 within flow assembly 100.

Figure 3:
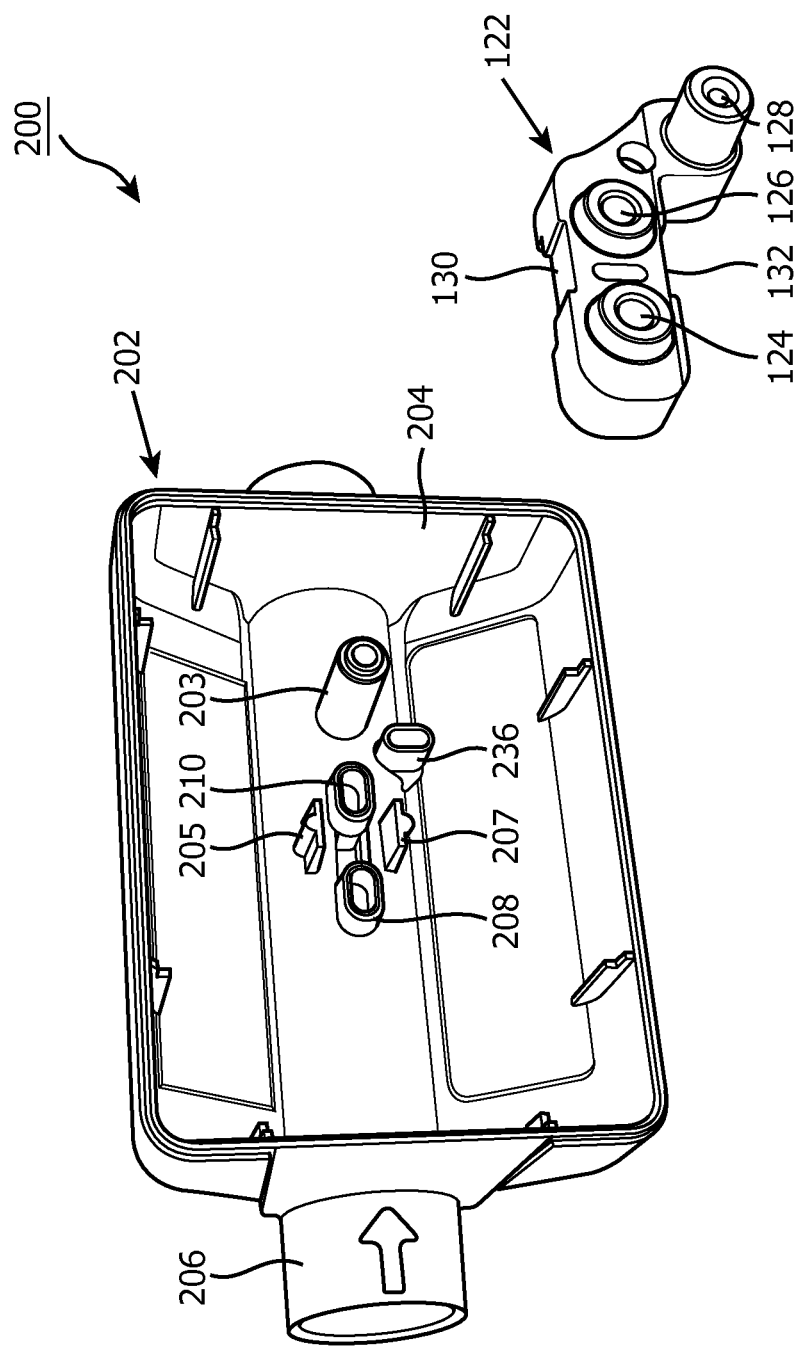
FIG. 3 is an exploded perspective view of a portion of the flow assembly of FIG. 2.
Figure 4:
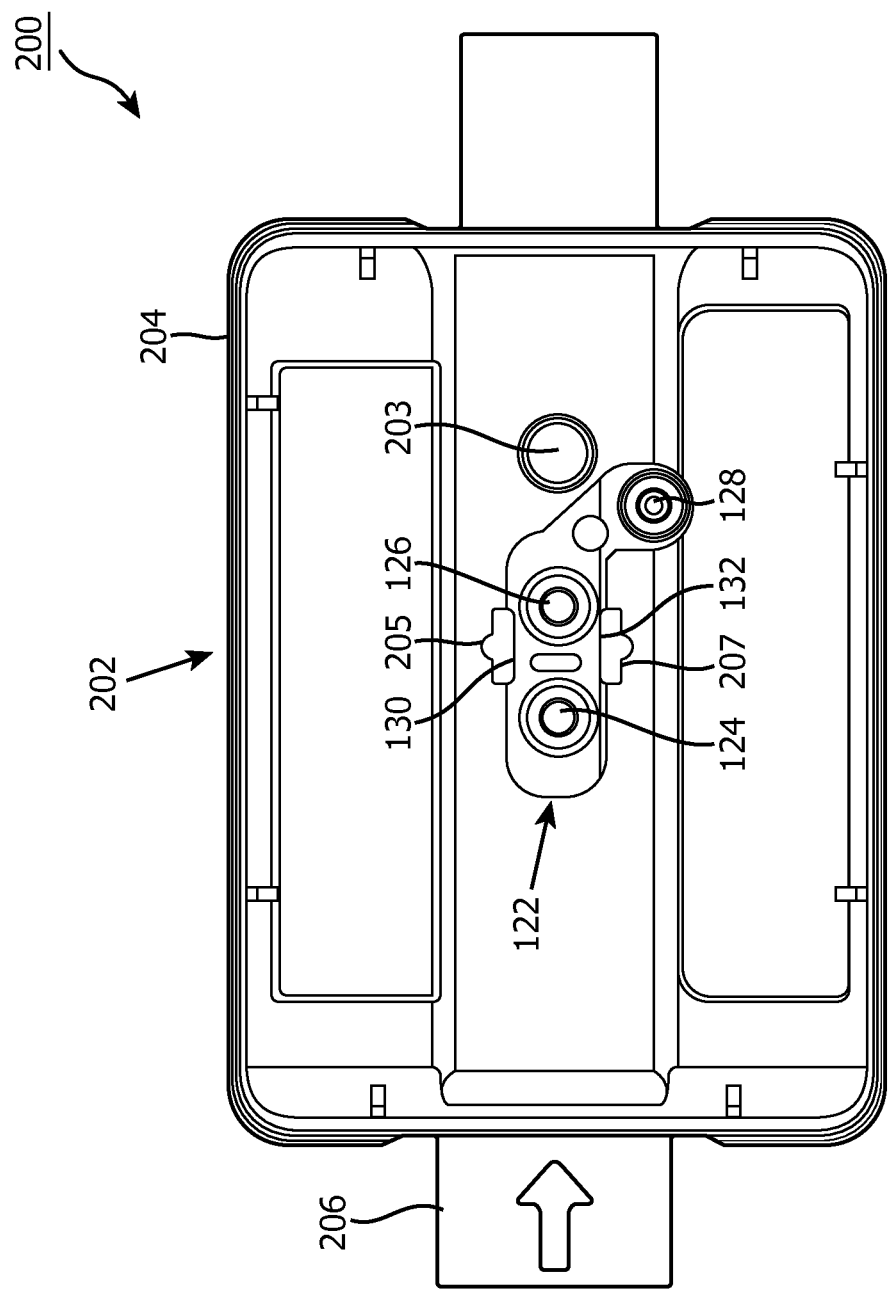
FIG. 4 is an assembled plan view of the portion of the flow assembly of FIG. 3.

FIG. 3 and FIG. 4 show an exploded view of sealing gasket 122 and flow member 200, and an assembled view of sealing gasket 122 and flow member 200, respectively. Sealing gasket 122 is coupled to the outside of conduit and operates to secure and properly position flow sensor 114 (FIG. 2) and pressure sensor 116 (FIG. 2) within flow assembly 100, in order that accurate measurements of pressure and volumetric flow rate of gas are taken. Referring to FIG. 3, body 202 further includes a number of stabilizing elements (see, for example, two stabilizing elements 205, 207) extending outwardly from gas conduit 206, a sensing conduit comprising a number of flow conduits (see, for example, two flow conduits 208,210), and a pressure conduit 236. Flow conduits 208,210 are spaced from each other and each extend generally transverse to gas conduit 206. Flow conduit 208 receives flow sensing component 118 (FIG. 2), and flow conduit 210 receives flow sensing component 120 (FIG. 2). Similarly, pressure conduit 236 is spaced from each of flow conduits 208,210 and extends generally transverse to gas conduit 206. Pressure conduit 236 receives pressure sensor 116. Sealing gasket 122 has a number of grooved regions 130,132.

It will be appreciated that grooved regions 130,132 fit between and engage stabilizing elements 205,207 in order to retain sealing gasket 122 on flow member 200 by a manual press-fit mechanism. In this manner, when cover 102 (FIG. 2) is connected to flow member 200, sealing gasket 122 remains fixed with respect to flow member 200. It follows that in operation, flow sensor 114 (FIG. 2) and pressure sensor 116 (FIG. 2) likewise remain fixed with respect to flow member 200. Additionally, thru holes 124,126,128 are advantageously aligned with respective conduits 208,210, 236 in order to allow respective sensors 114,116 access to the interior of gas conduit 206, as will be discussed in greater detail below.

Figure 5:
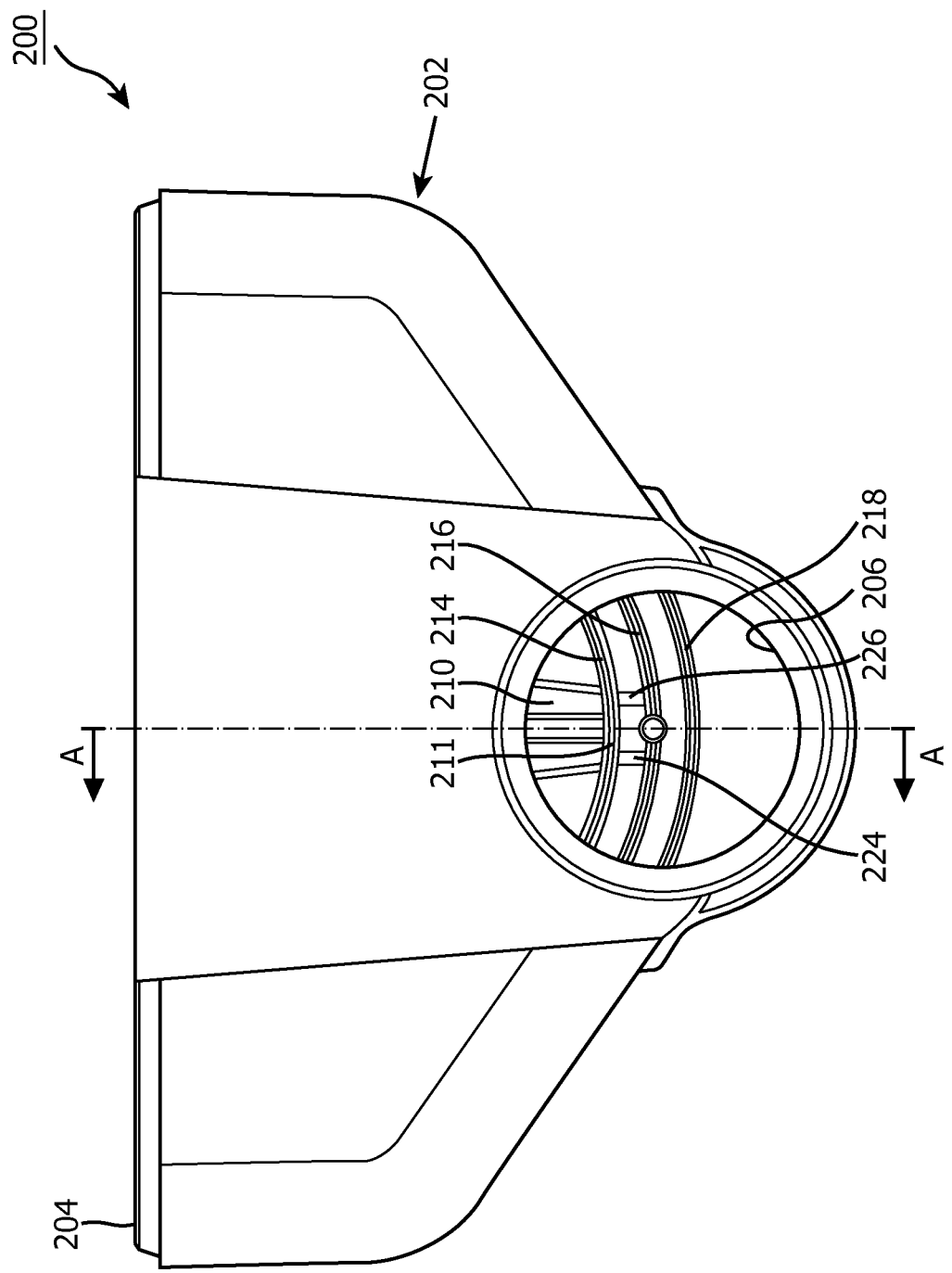
FIGS. 5 and 6 are different side elevation views of a flow member for the flow assembly of FIG. 2.
Figure 6:
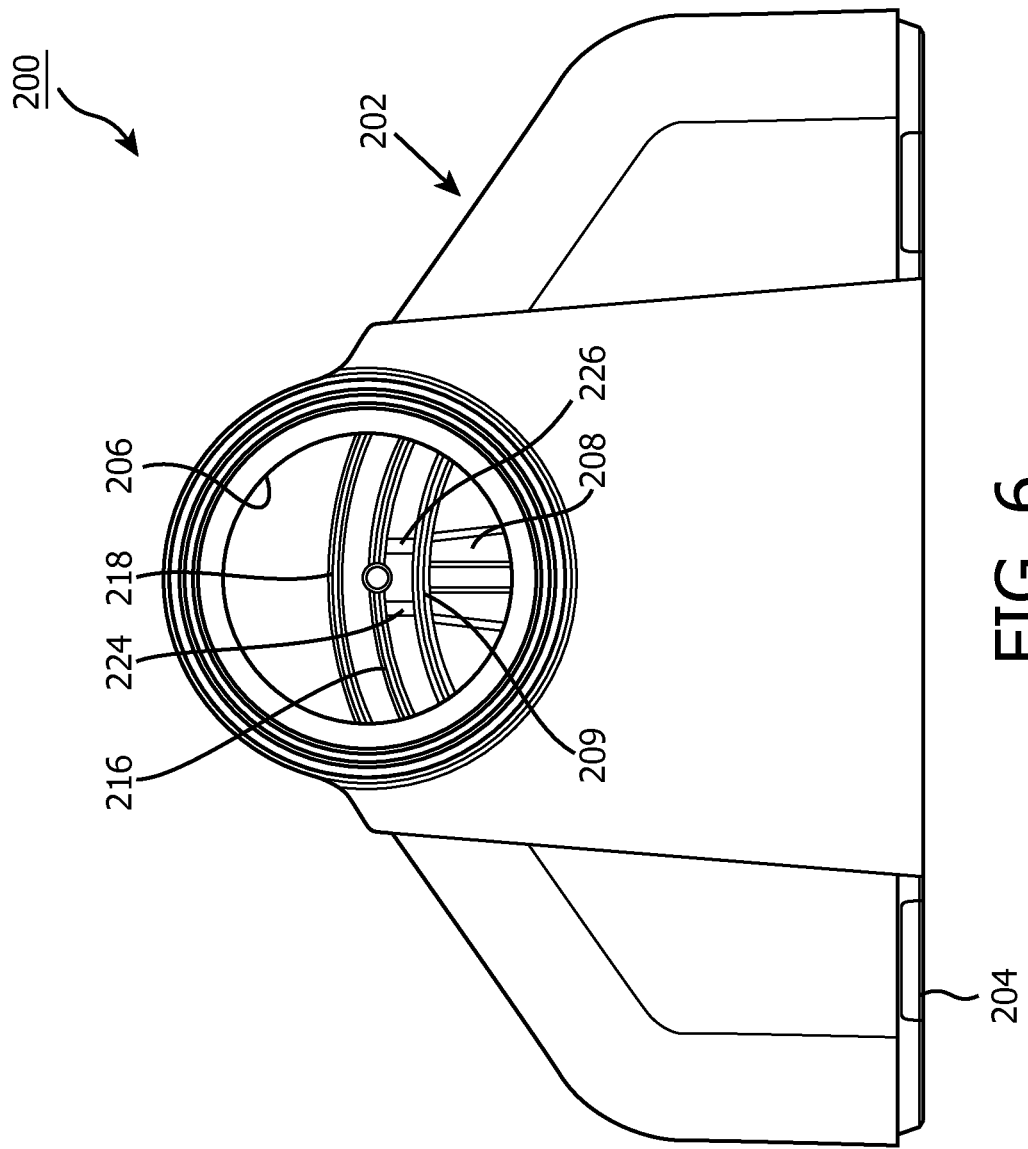

FIG. 5 and FIG. 6 show different views of flow member 200. As shown, body 202 further includes a number of walls (see, for example, three walls 214,216,218), each being concave facing each of flow conduits 208 (FIG. 6),210 (FIG. 5) and being located internal (i.e., located within or enclosed by) gas conduit 206. These walls form surfaces that are contoured in such a way that in any orientation water is encouraged to run "away" from the sensor ports. Wall 214 intersects flow conduits 208,210, which terminate proximate wall 214. Thus, breathing gas flowing through gas conduit 206 enters flow conduits 208,210 through wall 214. Wall 216 is between wall 214 and wall 218. Each of walls 214,216,218 are spaced from each other and are parallel with respect to each other.

Flow conduits 208 (FIG. 6),210 (FIG. 5) each terminate at a respective distal end portion 209,211 that is in fluid communication with gas conduit 206. Each distal end portion 209,211 is spaced from gas conduit 206 and is located internal (i.e., enclosed by) with respect thereto. In other words, flow conduits 208 (FIG. 6),210 (FIG. 5), which allow access to flow sensing components 118,120 (FIG. 2), each terminate at a location spaced from and internal with respect to the wall (i.e., the body, thickness, and/or physical structure) of gas conduit 206. That is, while flow conduits 208 (FIG. 6), 210 (FIG. 5) extend through the wall (i.e., the body, thickness, and/or physical structure) of gas conduit 206, distal end portions 209,211 are spaced a distance from the wall (i.e., the body, thickness, and/or physical structure) of gas conduit 206. Stated differently, a portion of flow conduits 208 (FIG. 6), 210 (FIG. 5) is located between distal end portions 209,211 and the wall (i.e., the body, thickness, and/or physical structure) of gas conduit 206.

FIG. 5 shows an elevation view of flow member 200 when flow assembly 100 (FIG. 1 and FIG. 2) is oriented right side up. When flow assembly 100 (FIG. 1 and FIG. 2) is in this orientation, it will be appreciated that water expelled by gas flow generator 4 (FIG. 1) (e.g., without limitation, water supplied to breathing gas from humidification during therapy) is structured to flow below walls 214,216,218 (i.e., due to the force of gravity). Similarly, moisture in the gases exhaled by patient 10 (FIG. 1) will likewise collect below walls 214,216,218 due to the force of gravity. FIG. 6 shows an upside down orientation of flow member 200 (such as, for example, during misuse conditions when a patient knocks gas flow generator 4 (FIG. 1) over during therapy). It will likewise be appreciated that water expelled by gas flow generator 4 (FIG. 1) and/or moisture in the gases exhaled by patient 10 (FIG. 1) are structured to flow below each of walls 214,216,218 (i.e., due to the force of gravity) when flow member 200 is in this orientation.

Figure 7:
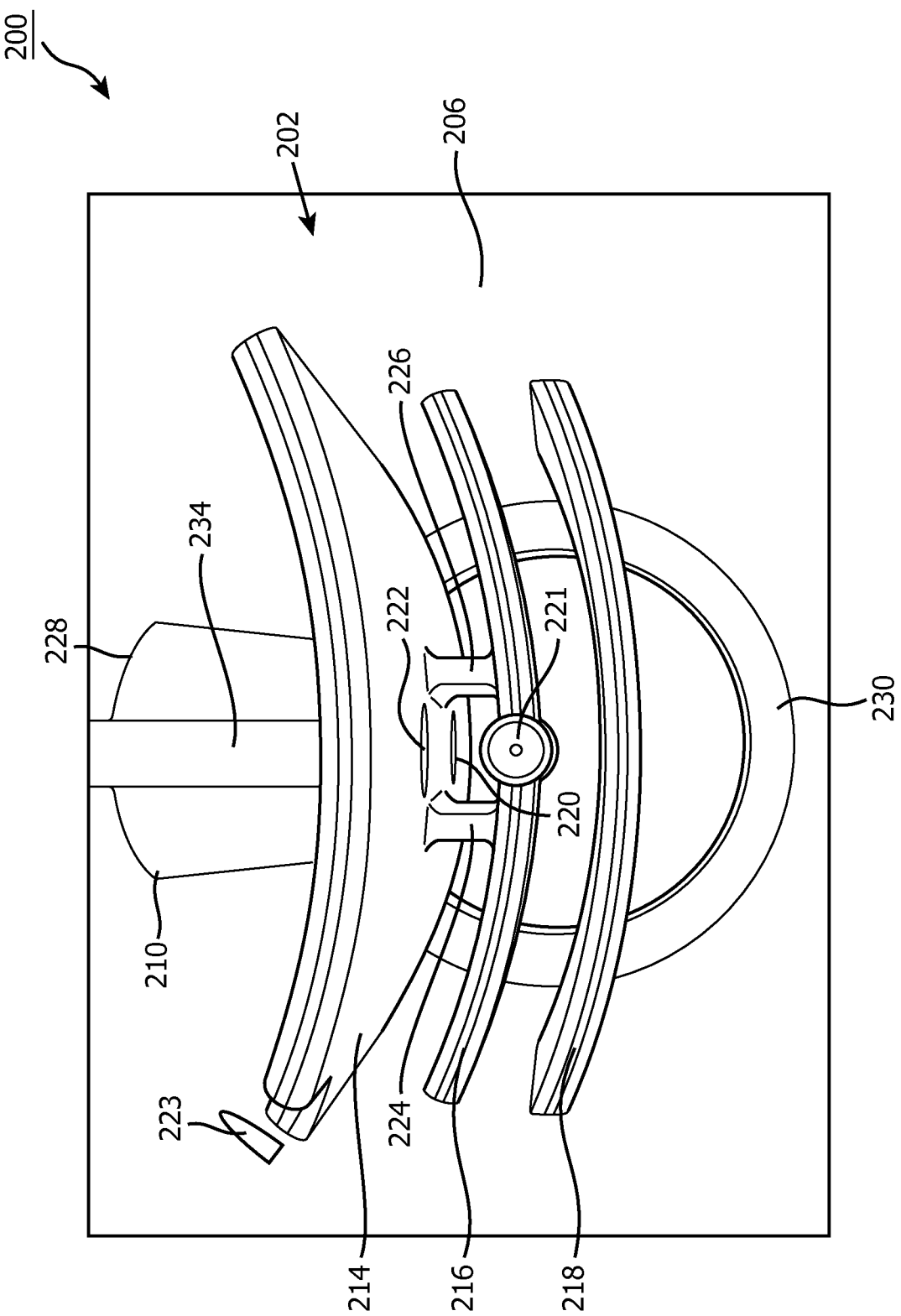
FIGS. 7 and 8 are different views of a portion of the flow member of FIGS. 5 and 6.
Figure 8:
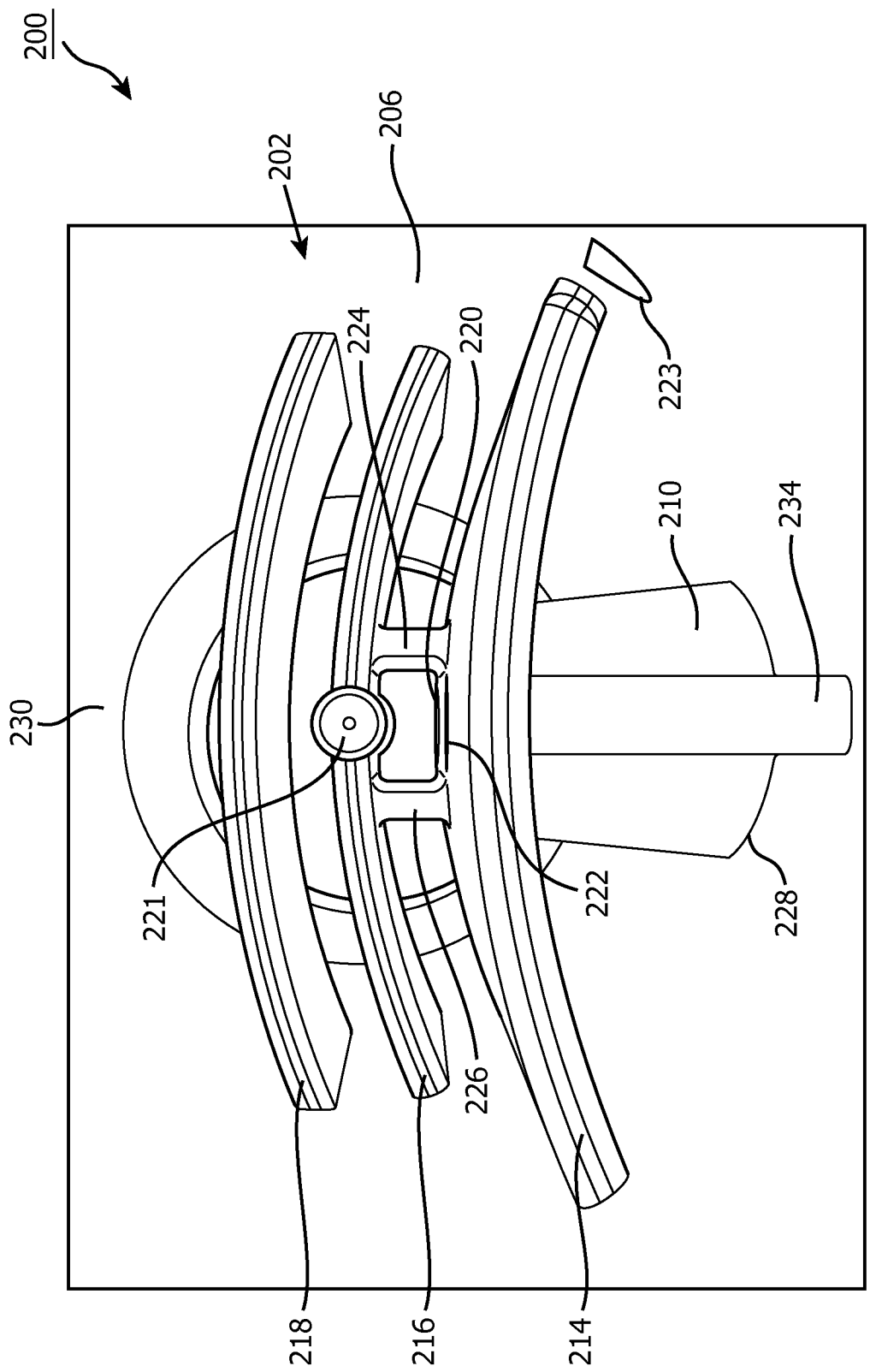

FIG. 7 and FIG. 8 show enlarged views of the interior of gas conduit 206. As shown, wall 214 has a number of ports 220,222. It will be appreciated that ports 220,222 extend entirely through the thickness of wall 214 in order to allow the respective flow sensing components 118,120 (FIG. 2) to be in fluid communication with the breathing gas in gas conduit 206. Furthermore, in any orientation (right side up (FIG. 7) or upside down (FIG. 8)), water and/or moisture is substantially less likely to enter ports 220,222 and thereby damage flow sensing components 118,120. More specifically, when flow assembly 100 (FIG. 1) is right side up (see, for example, flow member 200 in FIG. 7), water and/or moisture will collect below wall 218, thereby not entering either port 220 or port 222. Additionally, during misuse conditions, such as, for example, when flow assembly 100 (FIG. 1) is knocked upside down (see, for example, flow member 200 in FIG. 8), walls 216,218 will advantageously block and cause water and/or moisture to flow away from and below ports 220,222, thereby protecting flow sensing components 118,120 (FIG. 2).

In other words, in operation, the structural configuration of flow member 200, and the force of gravity will force water from humidification and/or moisture from exhaled gases to flow to the lowest location of gas conduit 206, which in either orientation (FIG. 7 or FIG. 8) is away from and below ports 220,222. More specifically, because ports 220,222 are spaced from gas conduit 206 and are located internal with respect thereto (i.e., are centrally located in gas conduit 206), and because walls 214,216,218 are concave facing towards flow conduits 208,210, flow sensing components 118,120 (FIG. 2) are protected from undesirable water ingress and/or moisture ingress through respective ports 220,222 and respective flow conduits 208,210. Stated differently, gravity forces water and/or moisture to collect below ports 220,222 when flow member 200 is right side up (FIG. 7), and the curvature of walls 214,216,218, together with the force of gravity force water to flow below ports 220,222 when flow member 200 is upside down (FIG. 8).

Continuing to refer to FIG. 7 and FIG. 8, gas conduit 206 has a port 223 extending through the thickness of gas conduit 206. It will be appreciated that port 223 is advantageously aligned (i.e., overlaying or allowing fluid to flow between pressure conduit 236 and the interior of gas conduit 206) with pressure conduit 236 and pressure sensor 116, thereby allowing pressure sensor 116 to measure the pressure of breathing gas in gas conduit 206. Additionally, pressure sensor 116 (FIG. 2) is water-safe and deadheaded, meaning that air within pressure sensor 116 (FIG. 2) provides protection from damage due to inadvertent water and/or moisture ingress during misuse conditions. In other words, pressure sensor 116 (FIG. 2) is likewise protected from damage.

Figure 9:
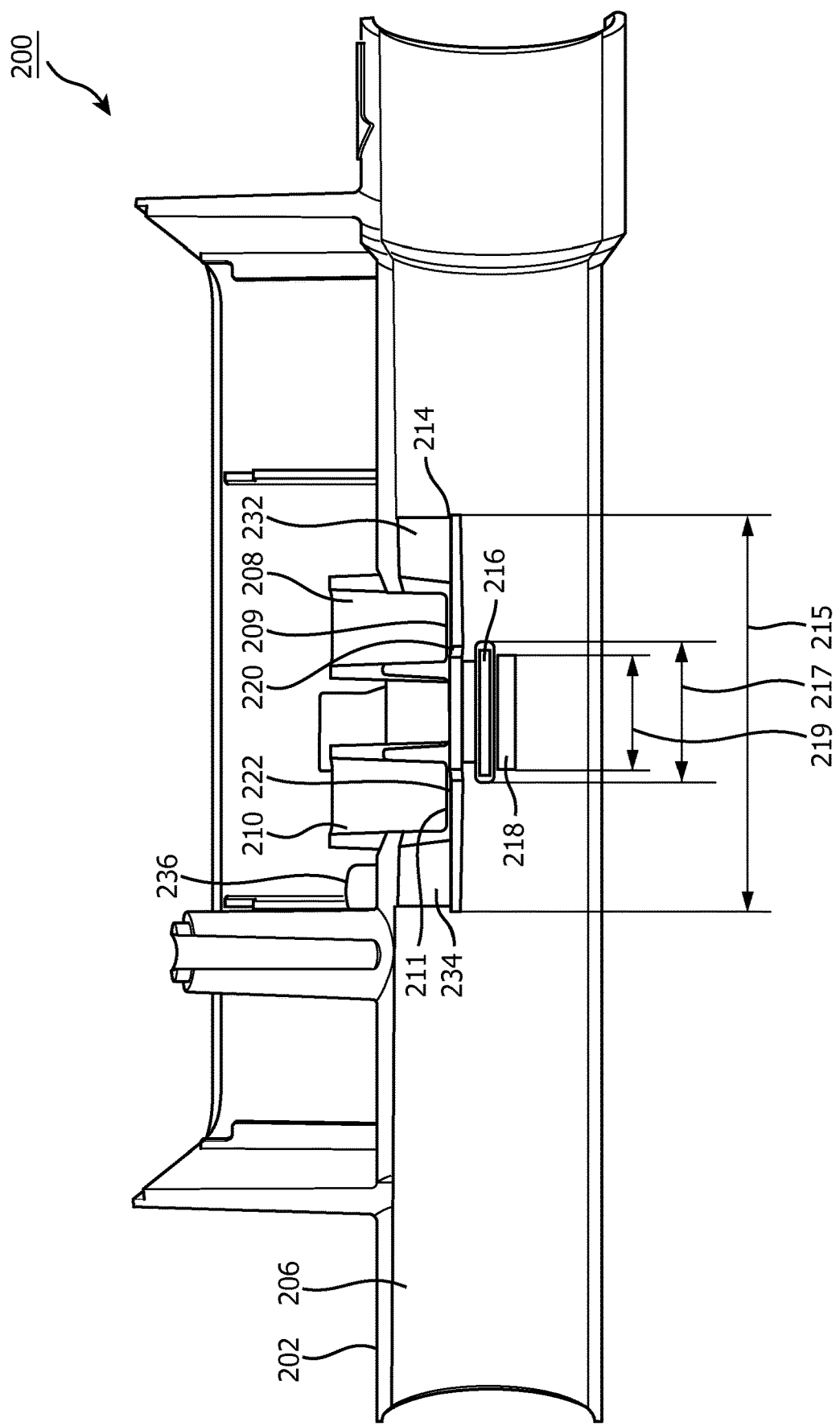
FIG. 9 is a section view of the flow member, taken along line A-A of FIG. 5.

FIG. 9 shows a section view of flow member 200. As shown, ports 220,222 are each located at a corresponding one of distal end portions 209,211 of flow conduits 208,210. Furthermore, walls 214,216,218 each extend longitudinally with respect to gas conduit 206 and each have a respective longitudinal length 215,217,219. Longitudinal length 215 is greater than each of longitudinal lengths 217,219. Thus, breathing gas entering gas conduit 206 will first begin to pass over wall 214, which is longer than each of walls 216,218 and has end portions that are each located closer to the respective ends of gas conduit 206. In this manner, wall 214 operates to lessen the turbulence of the breathing gas, thereby allowing the breathing gas to be more laminar as it approaches ports 220,222, advantageously resulting in more accurate flow readings for flow sensing components 118,120 (FIG. 2). Additionally, body 202 further includes another number of walls 232,234 each extending from and being generally perpendicular to wall 214. Walls 232,234, like walls 214,216,218, extend longitudinally with respect to gas conduit 206. Wall 232 extends from flow conduit 208, and wall 234 extends from flow conduit 210. In a similar manner as wall 214, walls 232,234 advantageously operate to make the flow of breathing gas entering and exiting gas conduit 206 more laminar, in order that readings taken by flow sensing components 118,120 (FIG. 2) are more accurate.

Figure 10:
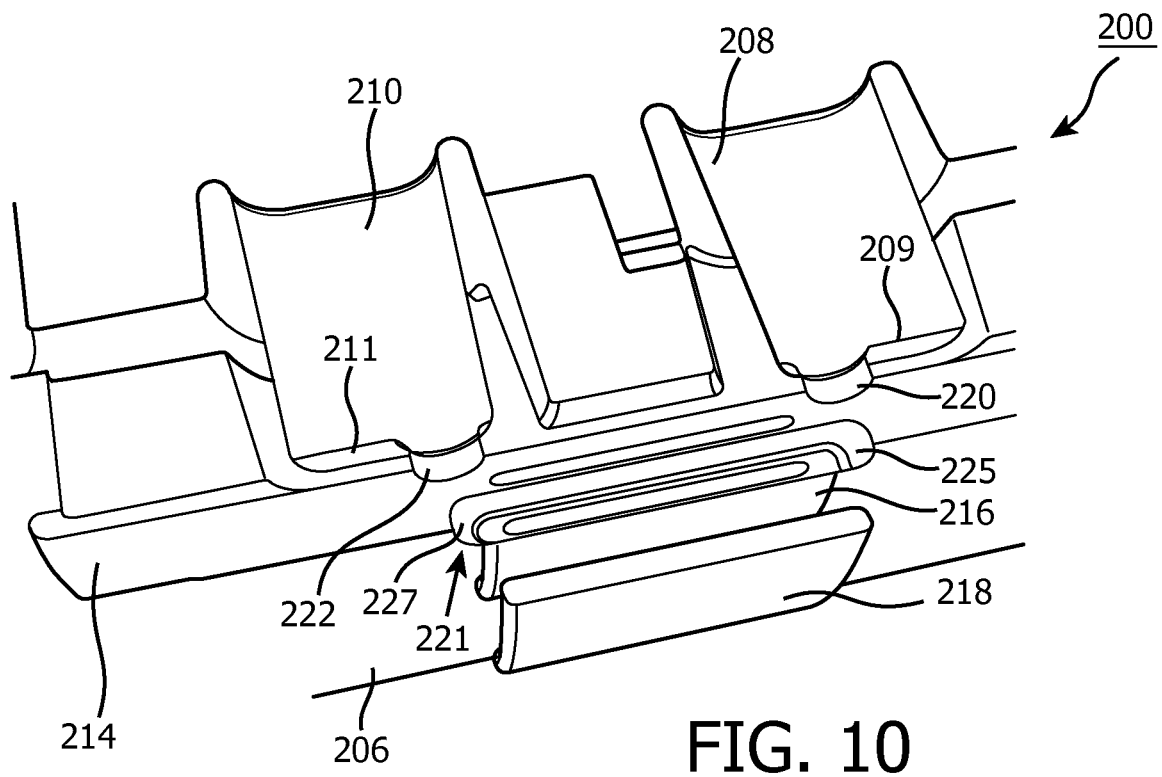
FIGS. 10, 11 and 12 are perspective views of different portions of the section view of FIG. 9.
Figure 11:
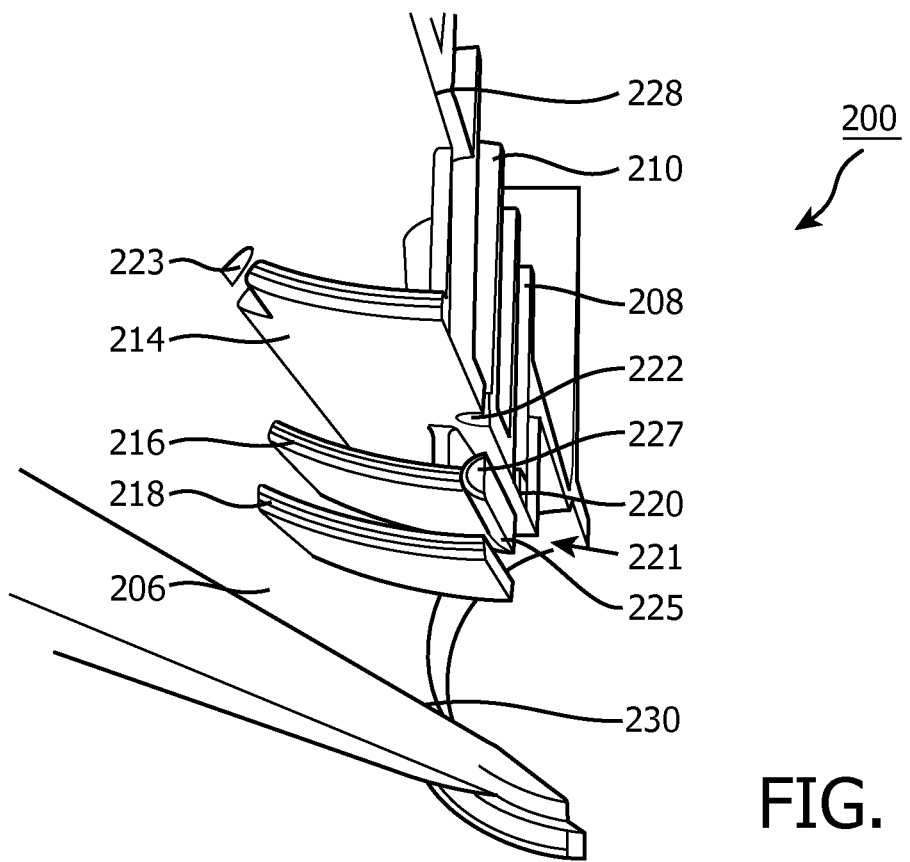
Figure 12:
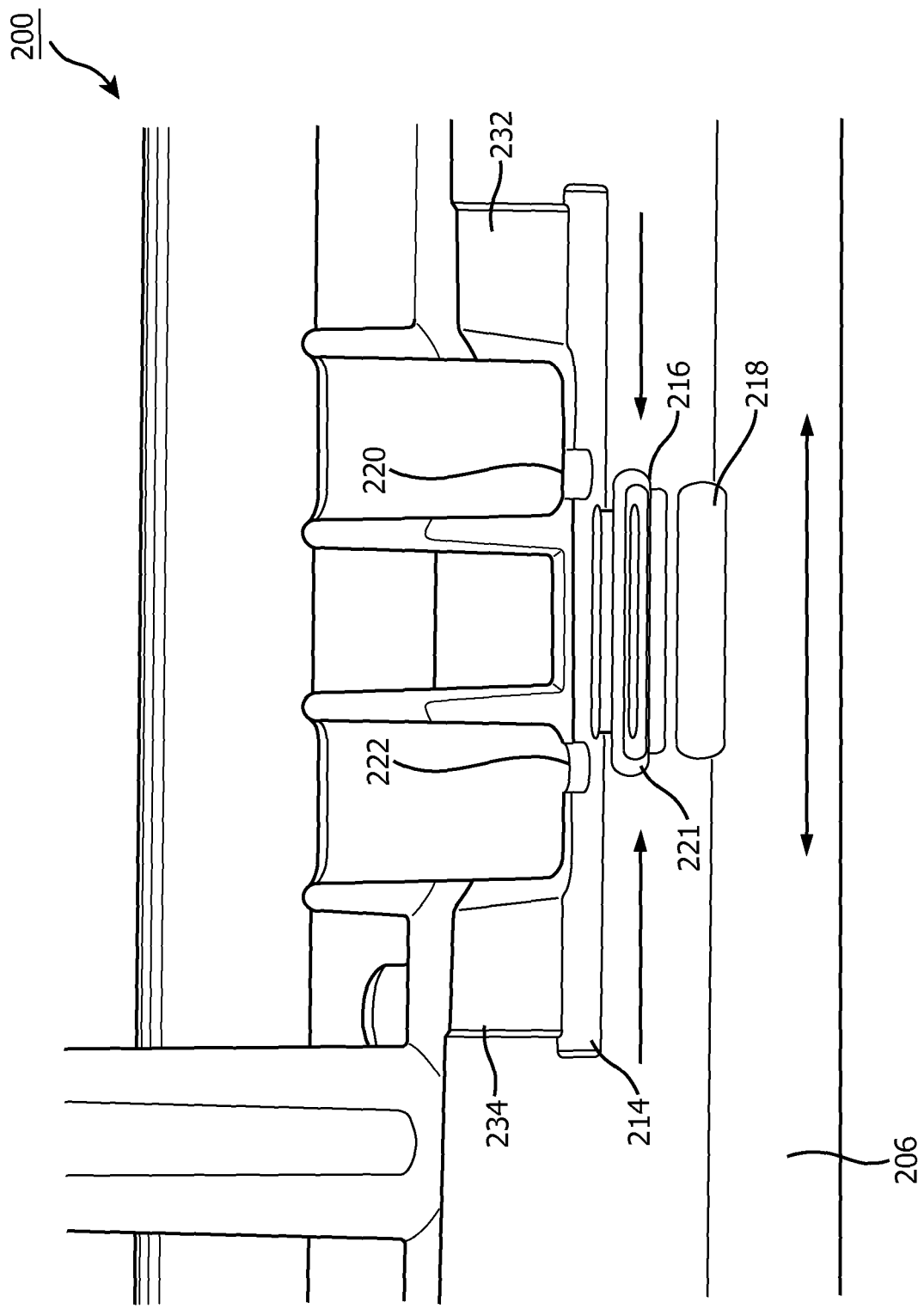

FIG. 10, FIG. 11 and FIG. 12 are different views of portions of FIG. 9. Referring to FIG. 11, gas conduit 206 has a first side portion 228 and a second side portion 230 located opposite and distal from the first side portion 228. As shown, flow conduits 208,210 each extend inwardly from first side portion 228. Walls 216,218 are at least partially located between second side portion 230 and each of ports 220,222 in order to substantially reduce the possibility of undesirable exposure of respective flow sensing components 118,120 (FIG. 2) through respective ports 220,222, as discussed above.

In order to create a pressure drop for flow sensing components 118,120 (FIG. 2), wall 216 advantageously includes a pressure drop element (see, for example, centrally located cylindrical-shaped air punch 221) extending longitudinally through gas conduit 206. As shown in FIG. 10, air punch 221 has rounded end portions 225,227 each being aligned with a corresponding one of ports 220,222. In the depicted orientations of FIG. 10 and FIG. 11, rounded end portions 225,227 are leach located directly below a corresponding one of ports 220,222. In this manner, when breathing gas passes through gas conduit 206 and engages respective rounded end portions 225,227, breathing gas is re-directed into a corresponding one of ports 220,222. More specifically, rounded end portions 225,227 cause a pressure drop as breathing gas moves through the path of flow sensing components 118,120 (FIG. 2).

Furthermore, referring again to FIG. 7 and FIG. 8, body 202 further includes another number of walls 224,226 each extending longitudinally with respect to gas conduit 206 and connecting wall 214 to wall 216. Ports 220,222 are each located between walls 224,226. In a similar manner as air punch 221, walls 224,226 advantageously operate to focus breathing gas entering gas conduit 206 toward ports 220, 222. More specifically, breathing gas entering gas conduit 206 engages the walls 224,226 and a portion of the breathing gas is focused toward ports 220,222. With better focused (i.e., more controlled, less turbulent, and/or more laminar) breathing gas passing over and into ports 220,222, measurements taken by flow sensing components are advantageously more accurate.

Referring to FIG. 12, it will be appreciated that the interior of gas conduit 206 is generally symmetrical. Thus, advantages associated with more accurate flow readings and/or a better protected flow sensor 114 (FIG. 2) apply equally to fluid flowing in either direction (i.e., entering from the left or right, with respect to the orientation depicted in FIG. 12). First, breathing gas entering from either direction will engage the same features (e.g., walls 214,216,218, air punch 221, walls 224,226 (FIG. 5 and FIG. 6), and/or either one of similarly shaped walls 232,234) in order to allow for more accurate flow readings. Second, water entering gas conduit 206 from the end opposite gas flow generator 4 (FIG. 1), such as for example, during cleaning and/or moisture from exhaled gases of patient 10 (FIG. 1), will advantageously be significantly less likely to enter ports 220,222 and damage flow sensor 114 (FIG. 2) in a similar manner as water due to humidification from gas flow generator 4 (FIG. 1) is from entering ports 220,222.

Additionally, flow member 200 is preferably made of a single piece of material, thereby simplifying manufacturing and reducing cost. More specifically, flow member 200 is preferably made by an injection molding process in which gas conduit 206 is made with only two core pull actions opposed to each other, while flow conduits 208,210 are formed in the standard draft direction of the tooling (not shown). It will, however, be appreciated that flow member 200 may be made by any suitable alternative process, provided the aforementioned features corresponding to protection of water and/or moisture ingress are employed.

Accordingly, it will be appreciated that the disclosed concept provides for an improved (e.g., without limitation, better protected against undesirable water and/or moisture ingress) pressure support system 2, and flow assembly 100 and flow member 200 therefor, which among other benefits, centrally locates and protects a number of ports 220,222 in a gas conduit 206 in order to substantially reduce the possibility of water and/or moisture ingress through a number of flow conduits 208,210.

While specific embodiments of the disclosed concept have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the disclosed concept which is to be given the full breadth of the claims appended and any and all equivalents thereof. In the claims, any reference signs placed between parentheses shall not be construed as limiting the claim. The word "comprising" does not exclude the presence of elements or steps other than those listed in a claim. In the device claim enumerating several means, several of these means may be embodied by one and the same item of hardware. The mere fact that certain measures are recited in mutually different dependent claims does not indicate that a combination of these measures cannot be used to advantage.

REFERENCE SIGNS LIST

2 Pressure support system
4 Gas flow generator

6 Patient interface device
8 Conduit
10 Patient
100 Flow assembly
102 Cover
103 Thru hole
104 Coupling member
110 Sensing assembly
114 Flow sensor
116 Pressure sensor
118 Flow sensing component
120 Flow sensing component
122 Sealing gasket
124 Thru hole
126 Thru hole
128 Thru hole
200 Flow Member
202 Body
203 Cylindrical-shaped protrusion
204 Mounting portion
205 Stabilizing element
206 Gas conduit
207 Stabilizing element
208 Flow conduit
209 Distal end portion
210 Flow conduit
211 Distal end portion
214 Wall
215 Longitudinal length
216 Wall
217 Longitudinal length
218 Wall
219 Longitudinal length
220 Port
222 Port
224 Wall
226 Wall
228 Side portion
230 Side portion
232 Wall
234 Wall
236 Pressure conduit

The invention claimed is:

1. A flow member comprising:
a gas conduit for conveying a gas containing moisture,
a sensing conduit for allowing a sensing component outside the gas conduit to sense a property of the gas via the sensing conduit, and
a number of walls disposed internal to the gas conduit and extending longitudinally with respect thereto;
wherein the sensing conduit passes through an outer wall of the gas conduit and terminates at a distal end portion thereof inside the gas conduit at a port disposed in a first wall of the number of walls, the distal end portion and the port disposed in the first wall being spaced a distance from the outer wall of the gas conduit to reduce an amount of moisture contained in the gas entering into the sensing conduit, and
wherein the number of walls are concave contoured in a direction perpendicular to the longitudinal extension thereof in such a way that in right side up and upside down orientations gravity will force moisture to flow away from the distal end portion of the sensing conduit at the port disposed in the first wall of the number of walls.

2. The flow member of claim 1 wherein a second wall and a third wall of the number of walls are spaced from each other and from the first wall to block and cause moisture to flow away from and below the port; and wherein the second wall is disposed between the first wall and the third wall.

3. The flow member of claim 2 wherein the first wall, the second wall, and the third wall are oriented parallel with one another.

4. The flow member of claim 2 wherein each of the first wall, the second wall, and the third wall is concave facing the sensing conduit.

5. The flow member of claim 2 wherein the first wall has a first longitudinal length along the gas conduit;
wherein the second wall has a second longitudinal length along the gas conduit;
wherein the third wall has a third longitudinal length along the gas conduit; and
wherein the first longitudinal length is greater than each of the second longitudinal length and the third longitudinal length.

6. The flow member of claim 2 wherein the gas conduit has a first side portion and a second side portion disposed opposite one another;
wherein the sensing conduit extends inwardly from the first side portion;
wherein each of the second wall and the third wall is at least partially disposed between the second side portion and the port.

7. The flow member as claimed in claim 1, wherein the sensing conduit comprises a first flow conduit and a second flow conduit spaced along the gas conduit from the first flow conduit.

8. The flow member as claimed in claim 1, wherein the gas conduit and the sensing conduit are made of a single piece of material.

9. A flow assembly comprising:
a cover;
a sensing assembly comprising the sensing component; and
the flow member as claimed in claim 1, and further comprising a mounting portion enclosing the sensing assembly.

10. The flow assembly of claim 9 wherein the sensing assembly further comprises a pressure sensor; and
wherein the flow member further comprises a pressure conduit for allowing the pressure sensor to sense a pressure of the gas in the gas conduit.

11. The flow assembly of claim 10 wherein the sensing component comprises a first flow sensing component and a second flow sensing component;
wherein the sensing assembly further comprises a sealing gasket disposed on the gas conduit;
wherein the sealing gasket has a first thru hole, a second thru hole, and a third thru hole;
wherein the first flow sensing component is aligned with the first thru hole;
wherein the second flow sensing component is aligned with the second thru hole; and
wherein the pressure sensor is aligned with the third thru hole.

12. The flow assembly of claim 11 wherein the flow member further comprises a first stabilizing element and a second stabilizing element each extending outwardly from the gas conduit; and
wherein each of the first stabilizing element and the second stabilizing element engages the sealing gasket in order to retain the sealing gasket on the flow member.

13. A pressure support system comprising:
a patient interface device;
a gas flow generator structured to produce a flow of breathing gas for a patient; and
a coupling conduit and the flow assembly as claimed in claim 9 coupled between the gas flow generator and the patient interface device.

14. The flow member as claimed in claim 1, further comprising a second sensing conduit for allowing a second sensing component outside the gas conduit to sense a second property of the gas via the second sensing conduit, wherein the second sensing conduit passes through the outer wall of the gas conduit and terminates at a distal end portion thereof inside the gas conduit at a second port disposed in the first wall of the number of walls, the distal end portion of the second sensing conduit and the first wall being spaced a distance from the outer wall of the gas conduit to reduce an amount of moisture contained in the gas entering into the second sensing conduit.

15. The flow member as claimed in claim 14, further comprising a pressure drop element extending longitudinally through the gas conduit, wherein the pressure drop element includes first and second rounded end portions, wherein each of the first and second rounded end portions are aligned with and located directly below a corresponding one of the port and the second port in the first wall of the number of walls.

16. The flow member as claimed in claim 15, wherein the pressure drop element comprises a cylindrical-shaped air punch centrally located within the gas conduit.

17. The flow member as claimed in claim 16, wherein the number of walls comprises three walls, and the air punch is disposed within a second wall of the three walls.

18. The flow member as claimed in claim 1, further comprising a pressure drop element extending longitudinally through the gas conduit, wherein the pressure drop element includes first and second rounded end portions, wherein one of the first and second rounded end portions is aligned with and located directly below the port in the first wall of the number of walls.

19. The flow member as claimed in claim 18, wherein the pressure drop element comprises a cylindrical-shaped air punch centrally located within the gas conduit.

20. The flow member as claimed in claim 19, wherein the number of walls comprises three walls, and the air punch is disposed within a second wall of the three walls.

* * * * *